(12) United States Patent
Ellis et al.

(10) Patent No.: US 7,338,531 B2
(45) Date of Patent: Mar. 4, 2008

(54) TEXTILE PROSTHESIS

(76) Inventors: Julian Ellis, c/o Ellis Developments Limited 68 Carlton Road, Nottingham NG3 2AP (GB); Peter Butcher, c/o Ellis Developments Limited 68 Carlton Road, Nottingham NG3 2AP (GB); Alan McLeod, c/o Pearsalls Limited Tancred Street, Taunton, Somerset TA1 1RY (GB)

( * ) Notice: Subject to any disclaimer, the term of this patent is extended or adjusted under 35 U.S.C. 154(b) by 0 days.

(21) Appl. No.: 10/398,883

(22) PCT Filed: Oct. 11, 2001

(86) PCT No.: PCT/GB01/04512

§ 371 (c)(1),
(2), (4) Date: Jul. 10, 2003

(87) PCT Pub. No.: WO02/30324

PCT Pub. Date: Apr. 18, 2002

(65) Prior Publication Data

US 2004/0078089 A1    Apr. 22, 2004

(51) Int. Cl.
*A61F 2/02*         (2006.01)
*A61F 2/008*        (2006.01)

(52) U.S. Cl. .............................. 623/23.74; 623/13.19; 623/13.14

(58) Field of Classification Search ................. 623/1.5, 623/1.51, 13.14, 13.2, 23.74, 13.19
See application file for complete search history.

(56) References Cited

U.S. PATENT DOCUMENTS

| | | | | |
|---|---|---|---|---|
| 4,776,851 A | * | 10/1988 | Bruchman et al. | 623/13.11 |
| 4,790,850 A | * | 12/1988 | Dunn et al. | 623/13.19 |
| 4,946,377 A | * | 8/1990 | Kovach | 623/13.18 |
| 5,004,474 A | * | 4/1991 | Fronk et al. | 623/13.14 |
| 5,192,322 A | * | 3/1993 | Koch et al. | 623/13.2 |
| 5,540,703 A | * | 7/1996 | Barker et al. | 606/139 |
| 5,800,543 A | * | 9/1998 | McLeod et al. | 623/13.2 |
| 7,214,225 B2 | * | 5/2007 | Ellis et al. | 606/60 |
| 2004/0078089 A1 | * | 4/2004 | Ellis et al. | 623/23.74 |

FOREIGN PATENT DOCUMENTS

| | | | |
|---|---|---|---|
| EP | 0314412 | * | 10/1988 |
| EP | 0744162 | * | 11/1996 |
| WO | WO 90/11735 | * | 10/1990 |
| WO | WO 02/30306 A1 | | 4/2002 |

* cited by examiner

*Primary Examiner*—Paul B. Prebilic
(74) *Attorney, Agent, or Firm*—Jonathan D. Spangler

(57) ABSTRACT

A textile prosthesis comprising a unitary body of predetermined shape having structural integrity, the body including at least one anchorage body portion for attachment to an anatomical body part, the body being composed of a combination of binding yarns and tensile load bearing filaments, the binding yarns being located at least in the or in each of said anchorage body portions and being interconnected to one another by sewn stitches, the tensile load bearing filaments being located inbetween said stitches so as to be constrained to extend through said unitary body along predetermined pathways extending in one or more predetermined directions so as to render the body resistance to stretch when a tensile load is applied in said one or more predetermined directions.

30 Claims, 15 Drawing Sheets

TEXTILE PROSTHESIS

FIELD OF THE INVENTION

The present invention relates in particular, but not exclusively, to a textile prosthesis and a method of producing a textile prosthesis.

The prosthesis may be used to regenerate an external fleshy body part such as an ear or may be a surgical implant.

BACKGROUND OF THE INVENTION

In the design of textile surgical implants, it is often desirable to apply a tensile load to the textile structure. For example, in orthopaedic applications the textile implant may be used to replace a damaged ligament. Ligaments join bones to bones and during movement of the body, a load is applied to the ligaments. To anchor the replacement ligament in place, it may be convenient or desirable to use a screw fixation device to anchor the textile implant to the bone so that the load may be properly transferred across the joint.

With a conventional woven textile, if a screw is pushed through the interstices of the woven structure, any load that is applied to the textile will be concentrated at one part of the weave structure, often on a single weft yarn causing the loaded yarn to move within the woven structure causing the weave to become distorted and the point of fixation on the fabric to change. In order to prevent this structural distortion, a number of methods have been suggested to overcome this difficulty. These methods include the use of staples to straddle a number of warp ends of the fabric so concentrating the load on a greater number or width of weft fibres; grommets have also been used which spread the load, not only across the width of the woven fabric but also extending the load bearing down the length of the fabric. However, this approach still results in some distortion of the woven structure, particularly when spaces are forced in the fabric to pass a grommet through.

It is also known that tubular braided structures are difficult to fix in place using conventional screws. The fibres in such a structure are usually angled at between 30° and 60° from the longitudinal axis of the fabric; this permits distortion which is greater than occurs with woven fabrics (where the weft is at approximately 90° to the warp of the fabric), because less load is taken up by the yarn at an angle to the direction of the load.

It may also be necessary for the textile implant to be secured to soft tissue, such as muscle. It is therefore desirable for the textile implant to be capable of being mechanically secured to soft tissue, for example by suturing whilst being able to transfer tensile loadings to the tissue to which it is secured.

It may also be desirable for the textile implant to be capable of promoting tissue ingrowth in order to enable the implant to be biologically connected to the soft tissue.

SUMMARY OF THE INVENTION

A general aim of the present invention is to provide a textile prosthesis, in particular but not exclusively, a surgical implant, which is better able to accommodate tensile loadings with less structural distortion.

According to an aspect of the present invention there is provided a textile prosthesis comprising a unitary body of predetermined shape having structural integrity, the body including at least one anchorage body portion for attachment to an anatomical body part, the body being composed of a combination of binding yarns and tensile load bearing filaments, the binding yarns being located at least in the or in each of said anchorage body portions and being interconnected to one another by sewn stitches, the tensile load bearing filaments being located inbetween said stitches so as to be constrained to extend through said unitary body along predetermined pathways extending in one or more predetermined directions so as to render the body resistance to stretch when a tensile load is applied in said one or more predetermined directions.

BRIEF DESCRIPTION OF THE DRAWINGS

Various aspects of the present invention are hereinafter described with reference to the accompany drawings in which.

DESCRIPTION OF THE PREFERRED EMBODIMENTS

A textile prosthesis constructed in accordance with the principles of the present invention is schematically illustrated in FIGS. 1 to 5 and comprises a body 10 which is composed of binding yarns 30 which are interconnected by sewn stitches and tensile load bearing yarns 20 which are encased within the body by being located in-between the binding yarn stitches.

The sewn stitches of the binding yarns 30 and the placement of the tensile load bearing yarns 20 are preferably created using embroidery techniques on a computer controlled embroidery machine, such as a Tajima or Barudan embroidery machine.

Generally such a machine includes a sewing head located above a base fabric and a looper head located below the base fabric. The sewing head supplies a sewing thread which is preferably interlaced with a looper thread supplied by the looper head. Accordingly during the sewing operation a sewing thread is laid upon the upper surface of the base fabric and a looper thread is laid upon the lower surface of the base fabric. The base fabric is normally held in a frame which is moved under the control of the computer by a pantograph.

By this conventional technique any stitch may be placed at any point within the embroidery frame, and the yarn length portions between successive stitches may be positioned at any angle and be of any length, subject to the dimensions of the embroidery frame.

In the present invention the base fabric on which the embroidery is performed may be removed, preferably by dissolution in a suitable solvent, after completion of the embroidery operation in order to leave the textile prosthesis as a body having its own structural integrity.

Alternatively the base fabric may remain to provide additional structural or tensile support.

Figure 1:
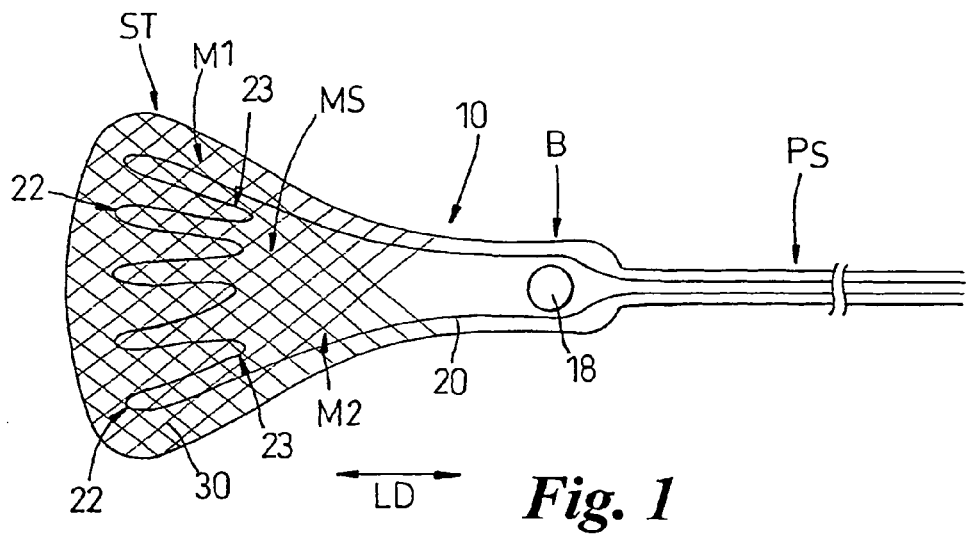
FIG. 1 is a diagrammatic representation of an example of a textile prosthesis according to the invention.

As indicated in FIG. 1, and byway of example, the body 10 is illustrated as including two anchorage portions ST and B which when attached to two separate anatomical body parts transmits loads between those parts in a direction LD.

In accordance with the invention, the body 10 may include any number of anchorage portions ST and/or B.

In certain applications, such as the creation of an artificial anatomical body part, the body 10 may include only one anchorage body portion and this may be either a body portion ST or a body portion B.

In accordance with the invention, the binding yarns 30 co-operate with the load bearing yarns 20 so that the load bearing yarns 20 are constrained to follow predetermined pathways through the body 10. In some areas of the body 10, in particular body portion ST, the binding yarns 30 may interact with one another to define a non-stretchable stable ground fabric structure, preferably of mesh-like form MS as shown in greater detail in FIGS. 2 to 5.

The ground fabric structure MS shown in FIGS. 2 to 5 includes a first series (FS) of stitches 31 of upper and lower binding yarns 30a, 30b having stitch lengths 35 extending in one direction and a second series (SS) of stitches 32 of upper and lower binding yarns 30c, 30d having stitch lengths 36 extending in a different direction, which in the illustrated example is 90° to the direction of the first series FS. It will be appreciated however that the directional angular relationship between the first and second series FS, SS may be greater or less than 90°.

Figure 3:
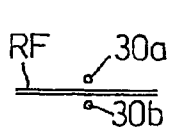
FIG. 3 is a section along line I-I in FIG. 2.
Figure 4:
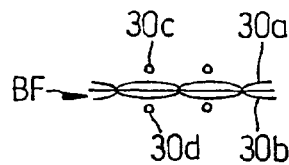
FIG. 4 is a section along line II-II in FIG. 2.

In FIGS. 3 and 4, a base fabric BF is shown into which the stitches 31, 32 are formed. Base fabric BF is subsequently removed to form the mesh-like ground fabric MS.

The stitches 31, 32 of the binding yarns 30 are spaced apart to define open spaces OS in the mesh-like fabric MS. The size of spaces OS may be changed to vary the density of the mesh-like fabric as desired by for example changing the stitch length between adjacent stitches 31 or adjacent stitches 32, changing the spacing between the series of stitches FS and SS, changing the size of the binding yarns 30 and/or introducing additional series of binding yarn stitches (i.e. have more than two series of stitches). For instance it is possible to create a relatively open mesh-like structure for promoting tissue ingrowth or a relatively closed mesh-like structure for inhibiting tissue ingrowth.

It is also possible by suitable choice of the stitch and/or yarn sizes to vary the flexibility of the mesh-like structure to provide the desired amount of flexure to the prosthesis. In other areas of the body the binding yarns 30 may interact so as only to constrain the load bearing yarns 20 along said pathways. In other areas the stitching together of binding yarns 30 may be performed so as to layer the binding yarns on top of one another in order to define a predetermined three dimensional shape to a predetermined region of the body 10.

Figure 2:
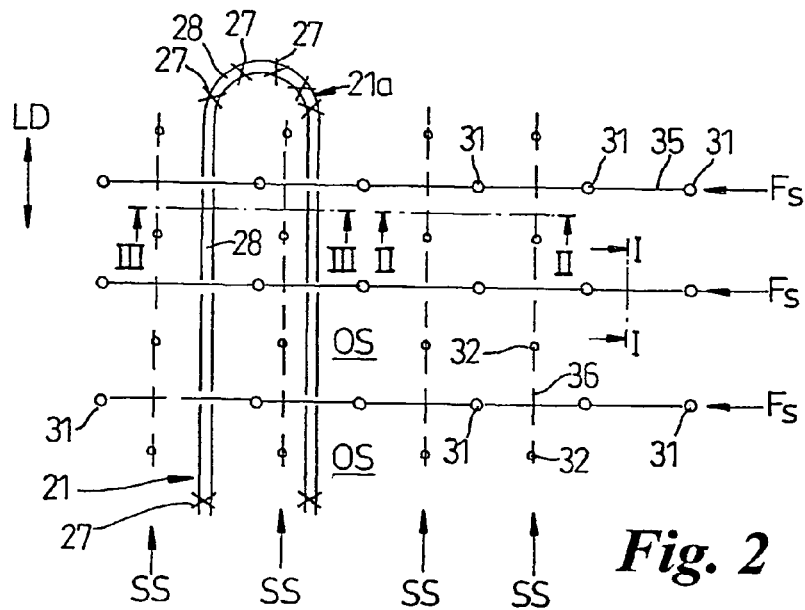
FIG. 2 is a diagram illustrating the inter-relationship between the binding and tensile load bearing yarns in accordance with a first aspect of the present invention.

As indicated in FIG. 2 the tensile load bearing yarns 20 are placed so as to have length portions 21 which extend in the direction of a predetermined tensile load bearing direction LD of the prosthesis body. As seen more clearly in FIG. 5, the tensile load bearing yarns 20 are located inbetween upper and lower stitch lengths 35 so as to be trapped within the mesh-like fabric MS.

This is achieved by securing the load bearing yarns 20 to the base fabric to follow its circuitous path and then after securing the load bearing yarn 20 to the base fabric, subsequently producing sewn stitches from the binding yarn 30. This ensures that the sewn stitches produced by the binding yarns 30 encase the previously laid load bearing yarns 20.

Prior to laying the load bearing yarns 20, it is envisaged that a precursor layer of binding yarns 20 may be stitched into the base fabric which are subsequently overlaid by the load bearing yarn 20.

The precursor layer may be of any desired shape and extent in order to provide desired reinforcement and/or increased density of the body in selected areas.

Preferably the stitches 31 are closely spaced to the outer sides of the yarns 20 so that the stitch lengths 35 of the binding yarns act to restrain lateral displacement of the tensile load bearing yarns 20. In addition, the stitches 31 and size of yarn 30 are preferably chosen so that the length portions 35 are closely spaced side by side along the length portions 21.

In order for the loading bearing yarns 20 to be trapped inbetween stitch lengths 35 it is necessary for the load bearing yarns 20 to be placed in position first and for the binding yarn 30 forming the first series of stitches FS to be sewn second.

Figure 5:
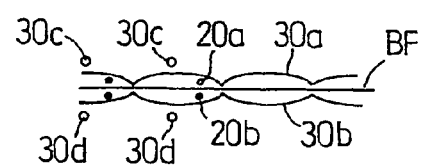
FIG. 5 is a section along line III-III in FIG. 2.

Placement of the load bearing yarns 20 may be performed by creating sewn stitches 27 between upper and lower yarns 20a, 20b (as seen in FIG. 5).

Preferably, the load bearing filament 20 is supplied from the looper of the embroidery machine and the thread supplied from the needle of the sewing machine is chosen to be much finer than the load bearing filament so that when stitches are formed between the needle thread and the load bearing filament 20, the load bearing filament remains flat against the base fabric and are not drawn through the base fabric by the needle thread. Alternatively, yarns 20 may be placed in position by a laying-in technique wherein the yarns 20 are temporarily held in position whilst sewn stitches 31 are created. With laying-in techniques, a single yarn end of yarn 20, or a desired multiple number of yarn ends of yarn 20 may be laid-in during each laying-in process.

As indicated above, in FIGS. 2 to 5 the load bearing yarns 20 are placed in position by creating stitches 27 between upper and lower yarns 20a, 20b.

The stitch lengths 28 between adjacent stitches 27 is preferably chosen to be the maximum distance required for ensuring correct directional placement of the yarns 20 during the embroidery process. In this respect, the stitch lengths 28 are relatively long along rectilinear length portions 21 whereas they are relatively short along curved length portions 21a.

By placing the yarns 20 in position by the embroidery process, it will be appreciated that the sewing of each single series of stitches 27 locates in place two yarns 20. Accordingly, prior to encasing the yarns 20 within the binding yarns 30, it will be appreciated that more than one series of stitches 27 may be created so that more than one pair of upper and lower yarns 20a, 20b are located inbetween each pair of stitch lengths 35.

In the example illustrated in FIGS. 2 to 5, only one series of stitches 31, i.e. the series Fs of stitches, is shown as extending across the load bearing yarns 20. It will be appreciated that additional series of stitches of binding yarns 30 may be provided so that the load bearing yarns 20 are encapsulated between more than one series of stitches.

As indicated in FIG. 1, the body 10 includes an anchorage portion ST for attachment to an anatomical body part defined by soft tissue such as muscle.

The anchorage portion ST of the present invention is preferably defined by a planar areal portion of stretch resistive fabric formed by said binding and load bearing yarns.

In the anchorage portion ST, the binding yarns 30 are preferably sewn together to define the mesh-like structure MS in which one series of stitches $M_1$ extend in one transverse direction across the load bearing yarn 20 and in which a second series of stitches $M_2$ extend in an opposite transverse direction across the load bearing yarn 20.

The mesh-like structure formed by the binding yarns 30, in effect defines a ground fabric structure which is relatively non-stretchable and through which the load bearing yarns 30 are constrained to pass along predefined pathways.

Preferably in the anchorage portion $ST_1$ the mesh-structure MS is open to promote tissue ingrowth such that the anchorage portion ST is able to be secured biologically to soft tissue.

In order to spread the load throughout portion $ST_1$ when the body 10 is placed under a tensile loading, the load bearing yarns 20 are laid along a circuitous route through the anchorage body portion ST such that at certain locations within the body the load bearing yarn 20 is looped relative to the load bearing direction LD to define opposed loops 22, 23. Accordingly, when a load is applied in the load bearing direction LD, the load tends to tighten the loops 22, 23 in direction LD and attempts to pull opposed loops 22 and loops 23 toward one another. However, such movement is resisted by the mesh-structure MS due to the loops 22, 23 being trapped in the mesh-structure MS, and if provided, by the interaction of stitches 27 of the load bearing yarns 20 with the stitches 31, 32 of the mesh structure MS.

In use an anchoring thread, such as a suture thread is passed through the mesh-like structure MS and into the soft tissue to which it is to be connected. The suture thread will therefore pass through the open spaces OS in the mesh-like structure and will secure the mesh-like structure to the soft tissue. After tissue ingrowth, the mesh-like structure will also be biologically secured to the soft tissue.

Accordingly after securance of the mesh-like structure to the soft tissue, the mesh-like structure will resist movement of opposed loops 22, 23 toward one another and, due to the load bearing yarn 20 being constrained along a circuitous path across a relatively large areal portion, loads are dissipated over a relative large area to the soft tissue.

The body 10 illustrated in FIG. 1 also includes an anchorage portion B which is intended to enable the body 10 to be anchored to a relatively hard anatomical body part such as bone by a fixing means such as a screw.

Figure 6:
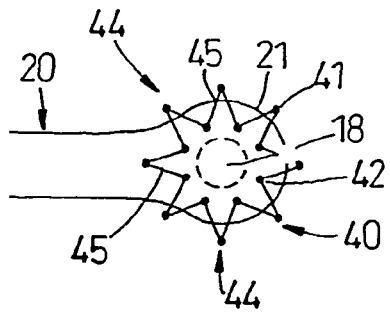
FIG. 6 is a diagram illustrating the inter-relationship between the binding and tensile load bearing yarns in accordance with a second aspect of the present invention, particularly suitable for forming an aperture.

The anchorage portion B includes at least one aperture 18 and the arrangement shown in FIG. 6 demonstrates how an aperture 18 may be formed for accommodating a fixing means such as a bone screw.

In FIG. 6, the tensile load bearing yarns 20 extend around the circumference of the aperture 18 and are held in position by a star shaped stitch formation 40, preferably formed from binding yarns 30. The star formation 40 is defined by successive stitches 41,42 which are spaced about the circumference of the aperture 18. The stitches 41,42 are spaced apart to embrace one or more yarns 20. The yarn portions 45 which extend between successive stitches 41,42 define reinforcement arms 44 which project radially outwardly from the aperture 18. Accordingly when the prosthesis body is exposed to a tensile load, the yarn length portions 45 tend to be placed in tension to resist the applied load whilst maintaining anchorage of the yarns 20. In FIG. 6 the load bearing yarn 20 is illustrated as extending partly about the circumference of the aperture 18. It is envisaged that the load bearing yarn 20 may extend continuously around the circumference of the aperture 18 for one or more turns.

Figure 7:
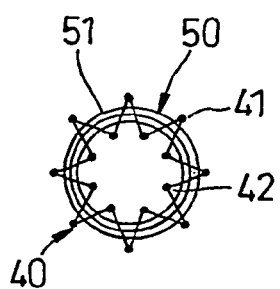
FIG. 7 is a diagram illustrating the incorporation of additional yarns for the formation of an aperture.

As an addition or an alternative to placement of yarns 20 about the periphery of the aperture 18, an additional reinforcement yarn 50 may be included as shown in FIG. 7. The reinforcement yarn 50 is placed so as to extend continually around the circumference of the aperture 18 for a desirable number of turns to define an annulus 51. The annulus 51 defined by the yarn 50 is enclosed between successive stitches 41,42. The annulus 50 assists in resisting deformation of the shape of the aperture 18 when tensile loads are applied.

Although the shape of the aperture in FIGS. 6 and 7 is shown as circular, it will be appreciated that the same structural arrangement of the yarns may be adopted for forming apertures of any desirable shape, such as slot shaped.

In addition, if desired the aperture 18 may be closed by fabric, for instance a mesh-like fabric created by binding yarns 30.

It will be appreciated that the aperture 18 constructed in accordance with FIG. 6 or 7 may be formed in a mesh-like structure defined by binding yarns 30. In such a case, the binding yarns defining the stitch formation 40 preferably interact with the binding yarns forming the mesh-like structure MS to anchor the stitch formation 40 to the mesh-like structure MS.

Optionally, as shown in FIG. 1, the body 10 may include a pull string or ribbon PS which is composed of the binding yarns 30 and load bearing yarns 20.

The load bearing yarns 20 of the string or ribbon PS are connected with the remainder of the body 10, preferably by forming a continuation of the load bearing yarns 20 passing through the remainder of the body 10, such that tensile loads applied to the ribbon PS are transmitted through the body 10. This is advantageous in that it enables a surgeon to attach a first anchorage portion (in the case of FIG. 1 anchorage portion ST) and then pull on the ribbon PS to tension the body 10 whilst attaching the second anchorage portion B. This ensures that the load bearing yarns 20 extending between the anchorage portion ST and B are placed under a desired amount of tension. The ribbon PS may then be severed and removed.

Alternatively, the ribbon PS may provide the surgeon with an alternative or additional means for securing the body 10 to an anatomical body part by tying the ribbon PS to that part.

It will be appreciated that the binding yarns 30 and load bearing yarns 20 may be combined to create many different types of body 10 made up of various combinations of anchorage portions, fabric constructions and/or three dimensional shapes tailored for specific implant applications.

Figure 8:
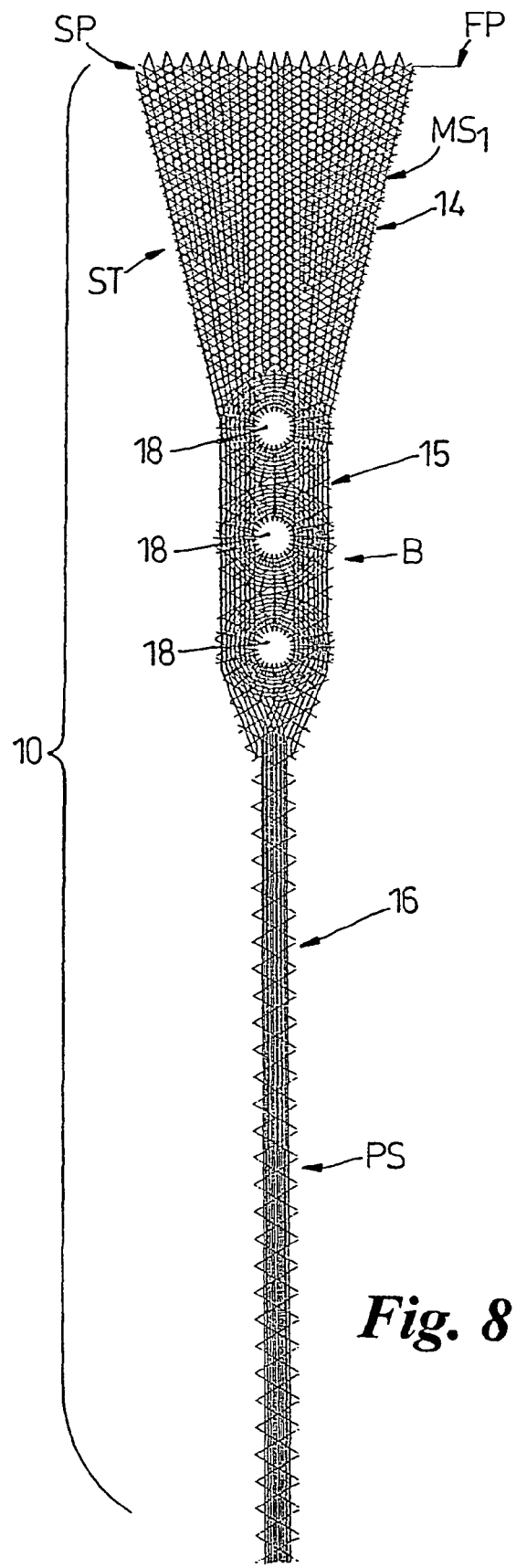
FIG. 8 is a diagrammatic plan view of a surgical implant according to a first embodiment of the present invention.

Described below, by way of example, are various specific embodiments. In FIG. 8 there is shown a first embodiment which is a surgical implant suitable for the repair of the shoulder of a human being, intended to reinforce the natural, but damaged tissue.

The implant comprises a body 10 which is generally planar and includes a first discrete body portion 14, a second discrete body portion 15 and a third discrete body portion 16.

The first body portion 14 defines an anchorage body portion ST, comprising a mesh-like structure $MS_1$ formed from binding yarns 30 in which load bearing yarns 20 are trapped. The anchorage portion ST is intended to be sutured to the natural tendon material forming the rotator cuff of the shoulder.

The body portion 15 defines an anchorage body portion B and preferably includes three apertures 18 each of which enable a bone screw to pass therethrough for securing the body portion 15 to the humeral bone. Three apertures 18 are provided in order to provide alternative sites for the bone screw and/or provide a plurality of sites for enabling more than one bone screw to be used.

It will be appreciated that the number of apertures 18 may be less or more than three. The apertures 18 each have a structure based upon that described with reference to FIGS. 6 and 7.

The body portion 16 defines ribbon PS to enable the surgeon to pull the body 10 after attaching body portion 14 so as to apply tension prior to attaching body portion 15.

After attachment of both body portions 14 and 15, body portion 16 may be removed by severance from body portion 15.

The body 10 is constructed using a plurality of yarns which are interconnected by sewn stitches.

Figure 9:
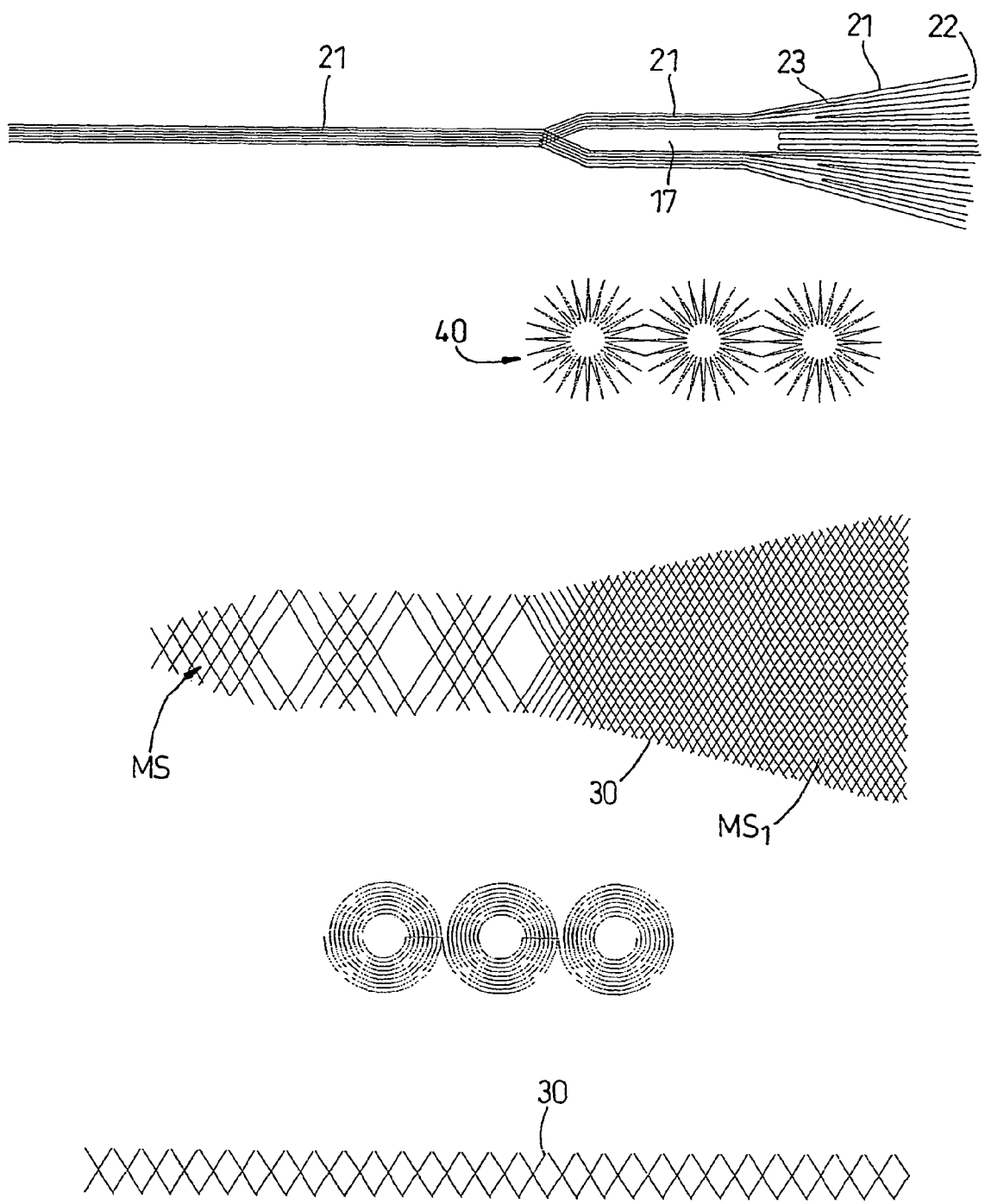
FIG. 9 is an exploded view of the implant of FIG. 8.

The structure of the implant 10 is more clearly shown in FIG. 9.

The tensile load bearing yarn 20 is placed upon the base fabric (not shown) by stitches 27 being formed between upper and lower yarns 20a, 20b at least at each point of change of direction for the yarn 20. This provides long length portions 21 of yarn 20.

Preferably as seen in FIG. 9, the yarn 20 runs continuously from the terminal end of body portion 14, through body portion 15 and into body portion 16.

Preferably the same yarn 20 (composed of one or more yarn ends which are either stitched together or laid-in) is placed along a circuitous route so as to pass continuously along body portions 14, 15 and 16 and to extend continuously across the area of body portion 14.

Preferably as seen in FIG. 8, yarn 20 starts outside body 12 at point SP and finishes outside body 12 at point FP.

The yarn 20 is placed within body portion 15 so as to define a window 17 corresponding to the location of apertures 18.

Annuli 51 of reinforcement yarn 50 are placed upon the yarn portions 21 of body portion 15 and star formations 40 are then placed so as to contain the spirals 51 and also the yarn portions 21.

Finally binding yarns 30 are placed in position by creating successive stitches to form the mesh-like structure MS, which encase the tensile load bearing yarns 20 as described above.

Figure 11:
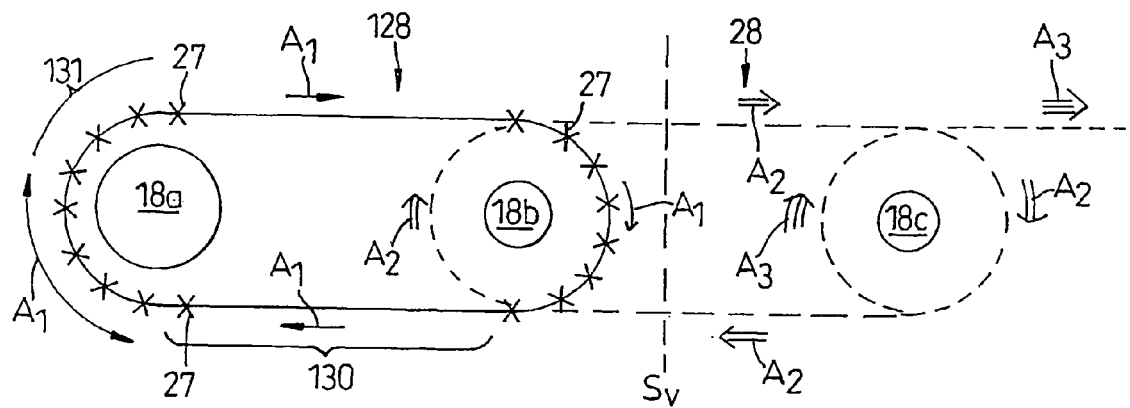
FIG. 11 is a diagram illustrating formation of chain-links for interconnecting a pair of apertures.
Figure 10:
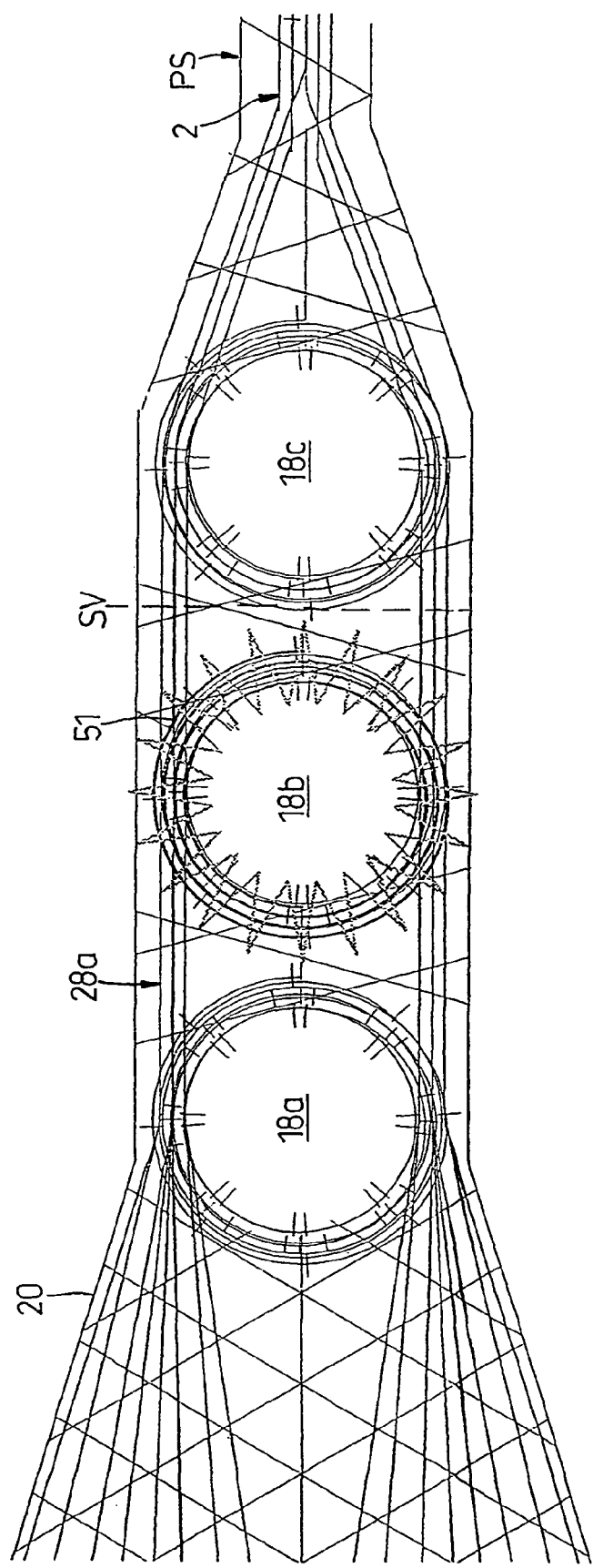
FIG. 10 is an enlarged part plan view of the implant of FIG. 8 showing an alternative structure.

A modified construction of the anchorage portion B for the first embodiment is illustrated in FIGS. 10, 11.

In FIG. 10, the load bearing yarn 20, instead of extending to define an elongate window 17, extend around the apertures 18 and are encased within star formations 40.

The yarn 20 is laid along a pathway which, in effect, defines chain-links 28 (shown schematically in FIG. 11) which are each joined about an aperture 18.

The connection between the chain-links 28 ensures that loads applied in direction LD between the anchorage body portion ST and pulling ribbon PS are transmitted through body portion 15 without causing distortion.

Preferably the chain-links 28 are each self-supporting such that if one chain link 28 is severed, the load bearing capability of the next adjacent chain link 28 is unaffected.

This means, for example, after attachment of the anchorage portion B by insertion of a bone screw through aperture 18b, the body portion 15 may be severed along line $S_v$ to enable the surgeon to remove the pulling ribbon PS and the remaining portion of body portion 15 attached thereto. After severance along line $S_v$, the chain-link 28a is still intact and so is able to transmit loads between aperture 18b and the anchorage portion ST.

Formation of each chain-link 28 is preferably achieved as illustrated schematically in FIG. 11.

A first chain-link 128 is formed by placing load bearing yarn 20 along a looped path as indicated by single arrows $A_1$ about a first pair of adjacent apertures 18a,b. The shape of the looped path is determined by location of stitches 27 between upper and lower yarns 20a, 20b and creates a relatively long rectilinear link portion 130 and a curved link portion 131 which extends approximately halfway about the circumference of aperture 18.

The yarn 20 is looped for a desired number of turns, for example 6 turns, and then is looped along the next adjacent looped path as indicated by double arrow $A_2$ about a second pair of adjacent apertures 18b, 18c. The process is then repeated to create the next chain-link 28.

Preferably star formations 40 and/or annuli 51 are provided to reinforce each aperture 18.

Figure 12:
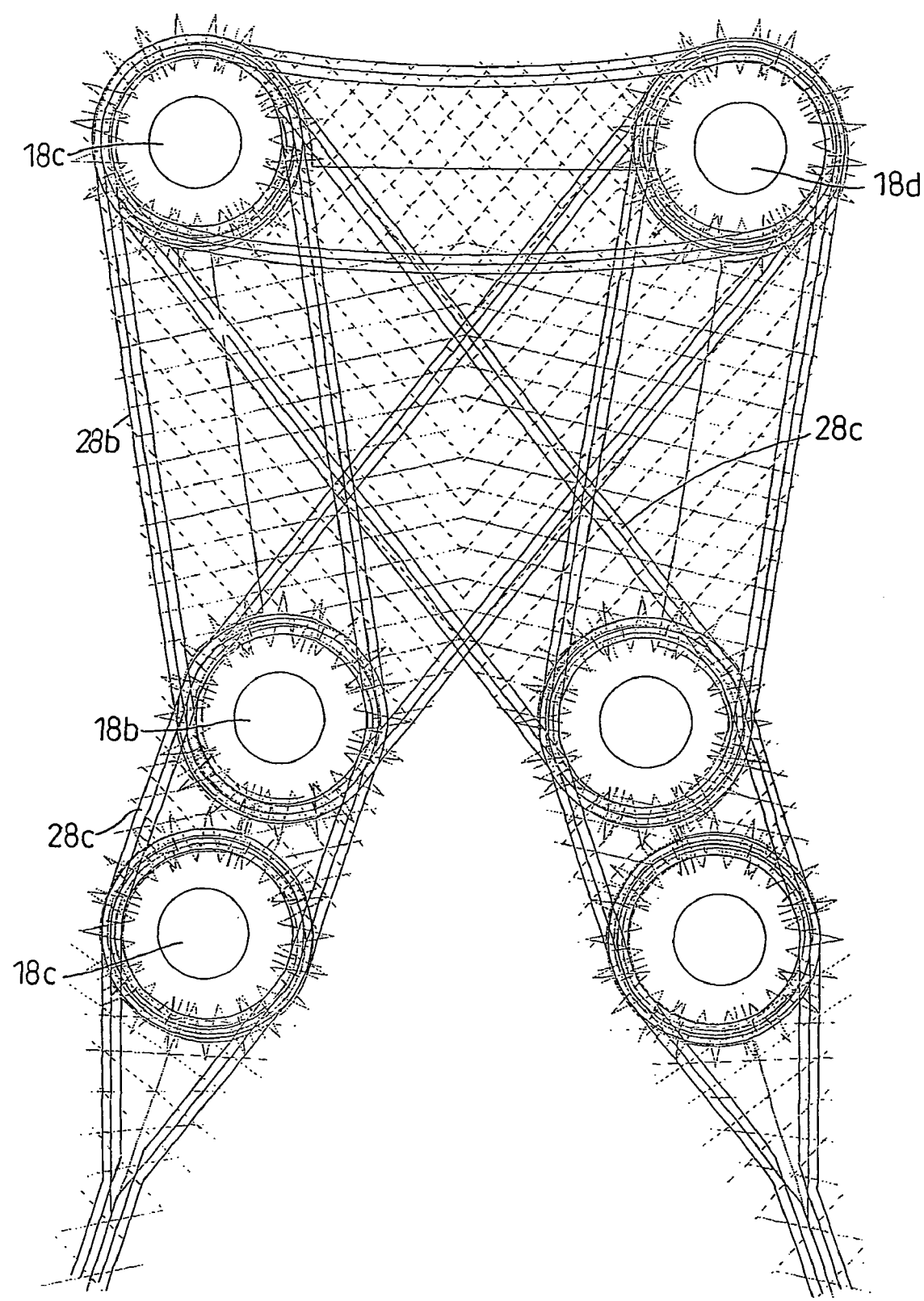
FIG. 12 is a diagrammatic plan view of a second embodiment according to the present invention.

In FIG. 12 a prosthesis 300 is illustrated which includes several anchorage apertures 18 which are inter-linked by chain-links 28 to provide a spread of loadings in several different directions.

In prosthesis 300, apertures 18a, 18b are interconnected by a chain-link 28a. Aperture 18b is inter-linked with two additional apertures 18c, 18d by chain-links 28b and 28c respectively.

Figure 13:
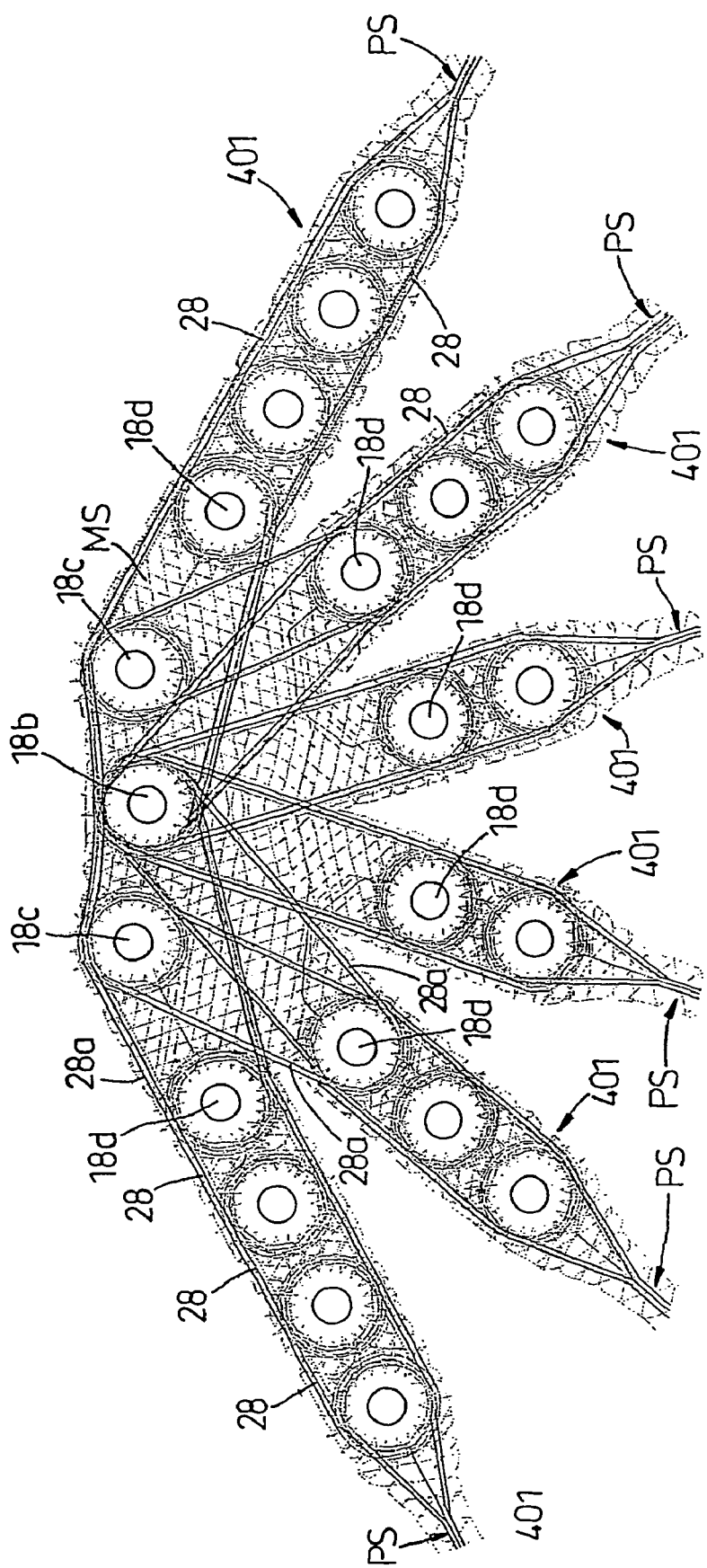
FIG. 13 is a diagrammatic plan view of a third embodiment according to the present invention.

In FIG. 13 a prosthesis 400 suitable for use as an anterior spinal plate is illustrated.

The prosthesis 400 includes six arms 401 each formed by a series of apertures 18 interconnected by chain-links 28.

The arms 401 radiate from three main fixation apertures 18a, 18b and 18c. These apertures 18a, 18b and 18c are attached to the LS vertebra of a patient and the arms 401 are attached to the sacrum. Due to the multiplicity of arms 401 and the plurality of apertures 18 they contain, it is possible to obtain good anchorage on the complex, three dimensional shape of the sacrum.

Preferably, as shown in FIG. 13, the end aperture 18d of each of the outer pair of arms 401 is preferably interconnected by a link 28a to at least two of the apertures 18a-18c in order to provide a desired spread of loadings.

Figure 14:
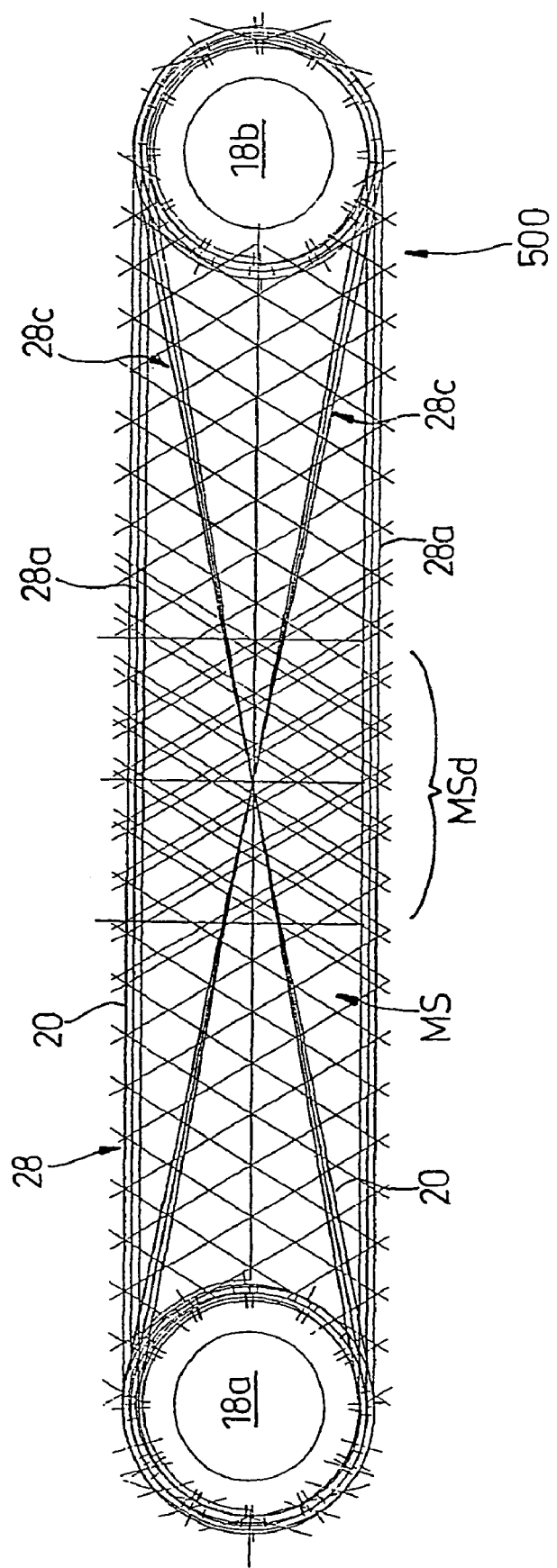
FIG. 14 is a diagrammatic plan view of a fourth embodiment according to the present invention.

In FIG. 14 there is illustrated a prosthesis 500 which is suitable for use as a spinal strap for securing together adjacent vertebrae in a spine.

The prosthesis 500 includes two apertures 18a, 18b which are interconnected by a chain-link 28 formed by load bearing filament 20. Load bearing filaments 20 are preferably also directed between the apertures 18a, 18b to define diagonal portions 28c. The diagonal portions 28c enable the strap to be twisted without losing its load bearing efficiency.

Preferably the load bearing filaments 20 are encased within a mesh structure MS defined by binding yarns 30. Preferably the central region MSd of the mesh structure is denser than the remainder of the mesh structure MS in order to resist the load bearing filaments cutting into the bone of the vertebrae of the spine. It is envisaged that the chain-link portions 28a which extend between apertures 18a, 18b may be omitted such that apertures 18a, 18b are interconnected by diagonal portions 28c only.

This is particularly advantageous if apertures 18a and 18b are not lying in the same two dimensional plane in that the diagonal links 18c facilitate an element of axial twist while maintaining overall tension between the apertures.

Figure 15:
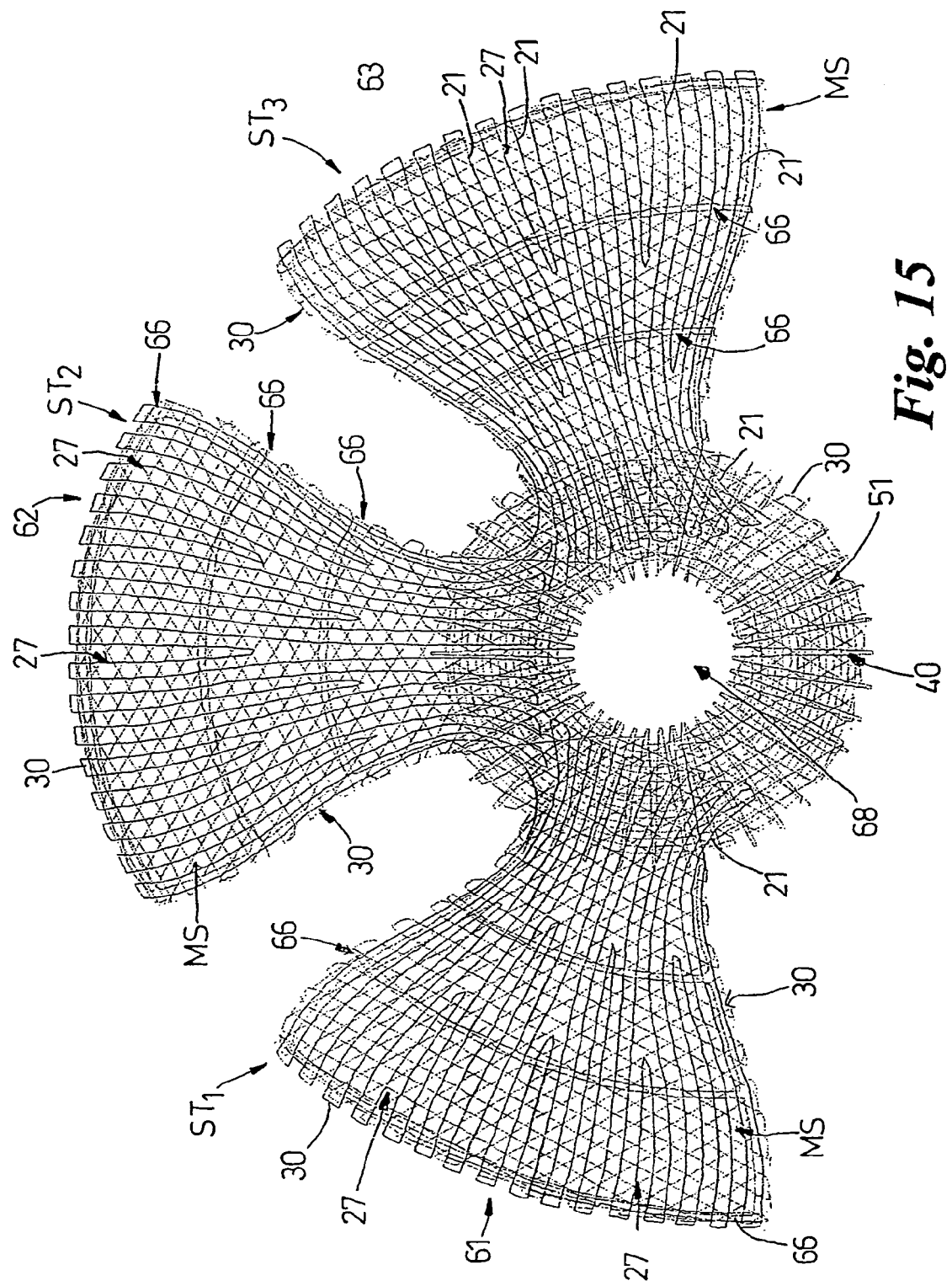
FIG. 15 is a diagrammatic plan view of a fifth embodiment according to the present invention.

In FIG. 15 there is shown a second embodiment 60 of the present invention which is a prosthesis having three anchorage body portions $ST_1$, $ST_2$, $ST_3$ defined by body portions 61, 62 and 63 each of which is designed to be attached to one of the three tendons of the rotator cuff. The body portions 61, 62 and 63 extend from an annular body portion 67 having a central hole 68. The annular body portion is formed from an annulus 51 and a star formation 40. The yarn 20 extends from each body portion 61, 62, 63 to be securely anchored by the star formation 40 and the binding yarns 30. The body portions 61, 62 and 63 are generally of fan shape and the yarn portions 21 of the tensile load bearing yarn are preferably provided with intermediate loop portions 27 to provide substantially equal spacing between yarn portions 21 despite the fanning out of the yarn portions as the fan shaped body portion becomes wider. Each of the body portions 61, 62 and 63 is preferably constituted by said mesh-like structure MS and preferably has additional reinforcement yarns 66 running circumferentially to the central hole 68. This additional reinforcement yarn 66 is intended to aid and assist the surgeon in placing the stitches to retain the wing of the implant to the tendon, and also indicate a site beyond which the device can be cut or trimmed to shape, the radially extending yarn portions 21 providing an extra strength area to minimise the possibility of any disintegration of the textile structure.

It will be appreciated that the region of the central hole 68, through which fits the stem of a modular humeral head, is reinforced using an annulus 51 and star formation 40 and these in combination with the binding yarns 30 hold the tensile load bearing yarns 20 running out into the body portions 61, 62, 63. This is desirable as the load bearing on the prosthesis 60 can be quite high in the first phase of the rehabilitation of the patient.

Figure 16:
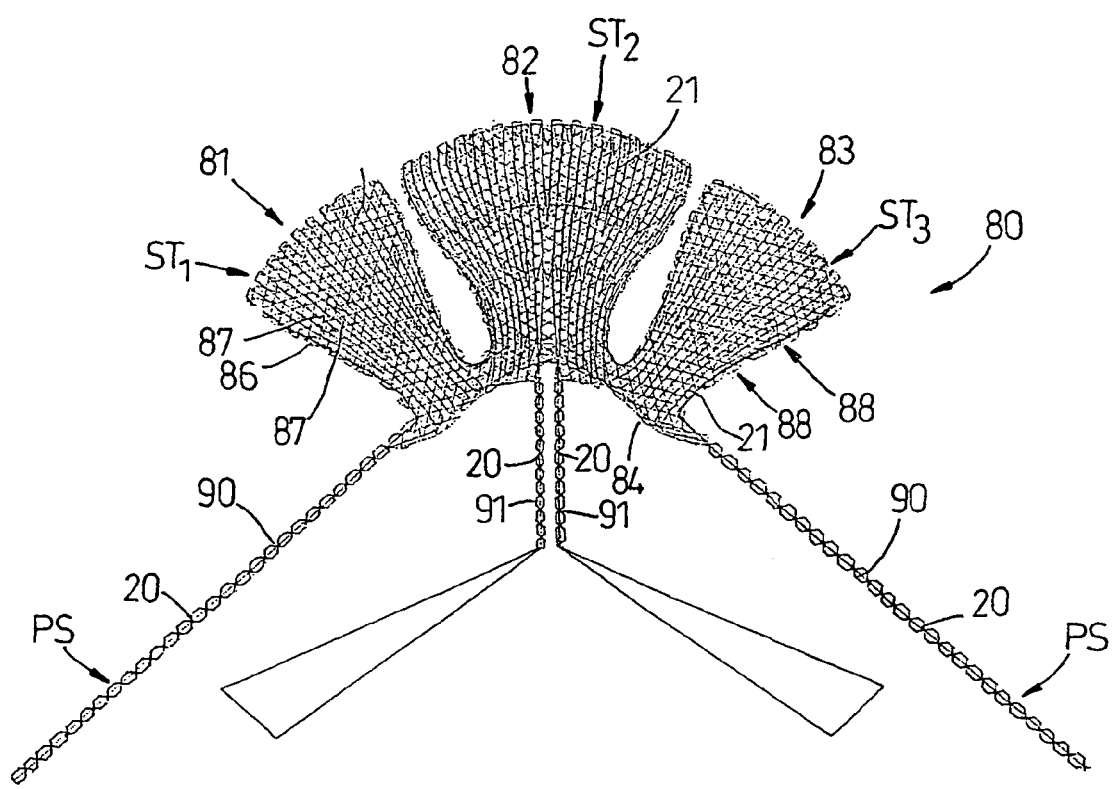
FIG. 16 is a diagrammatic plan view of a sixth embodiment according to the present invention.

The embodiment 80 illustrated in FIG. 16 is a multiple ligament reinforcement prosthesis. Prosthesis 80 includes three fan shaped anchorage body portions $ST_1$, $ST_2$, $ST_3$ defined by body portions 81, 82 and 83 which are joined together by a connecting body portion 84.

The body portions 81, 82 and 83 are of a similar structure to body portions 61, 62, 63 described above with the exception that the reinforcement yarn 66 is replaced by a reinforcement yarn 86 which is placed by a succession of stitches 87 which define arcuate zig-zag formations 88 which serve to prevent the fabric fraying after a surgeon has cut inbetween the formations 88. Preferably the yarn 86 has a contrasting colour to the other yarns in order to give the surgeon an easily recognisable guide for cutting.

Preferably the prosthesis 80 includes two arm portions 90 which form pulling ribbons PS connected to body portion 84. Load bearing yarns 20 extend continuously through both arm portions 90 and the connecting body portion 84. Arm portions 90 assist in the securing of the textile prosthesis to a metal prosthesis anchored within the bone of the patient. Optionally, additional ribbons 91 of similar structure to arms 90, depend from the connecting body portion 84 for further assisting in the anchoring of the textile prosthesis around the metal prosthesis.

Figure 17:
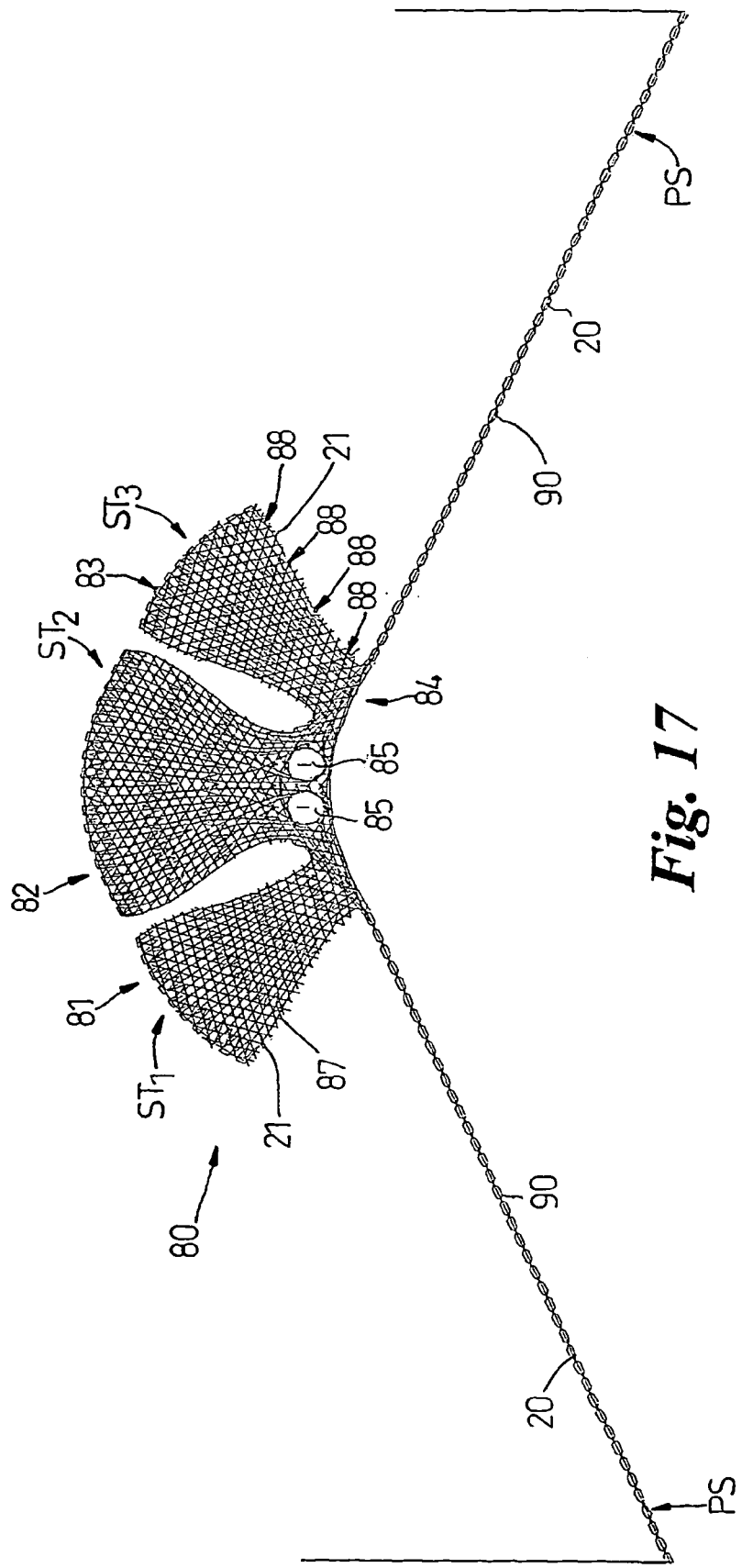
FIG. 17 is a diagrammatic plan view showing a modified version of the sixth embodiment.

As illustrated in FIG. 17 the prosthesis 80 may be modified to incorporate a pair of apertures 85 for enabling the prosthesis 80 to be connected to the metal prosthesis.

Figure 18:
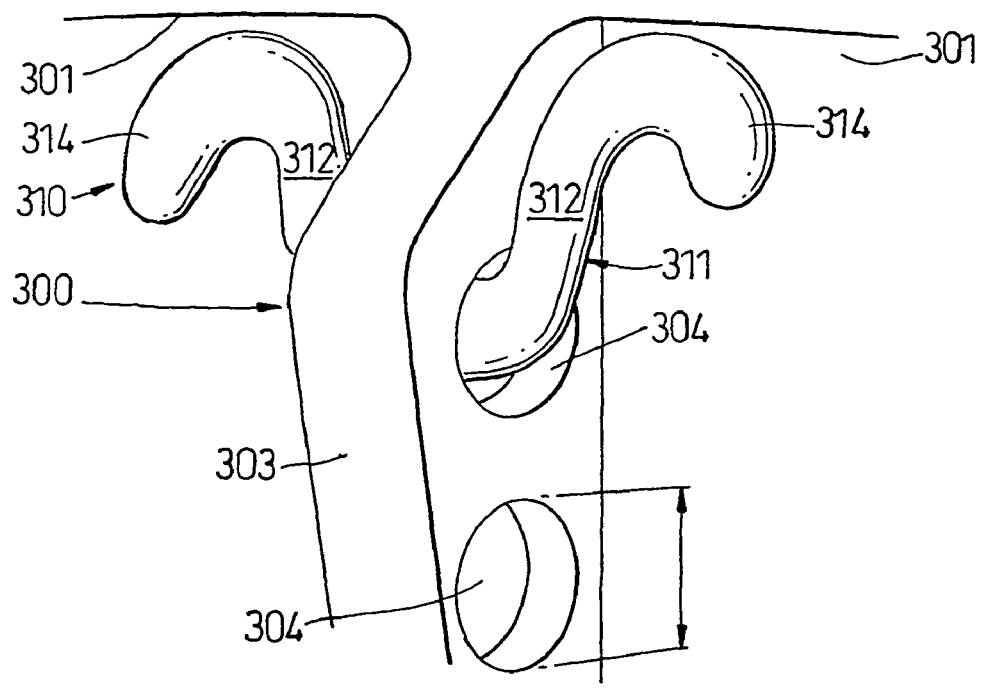
FIG. 18 is a schematic diagram of a metal prosthesis to which the sixth embodiment may be attached.
Figure 19:
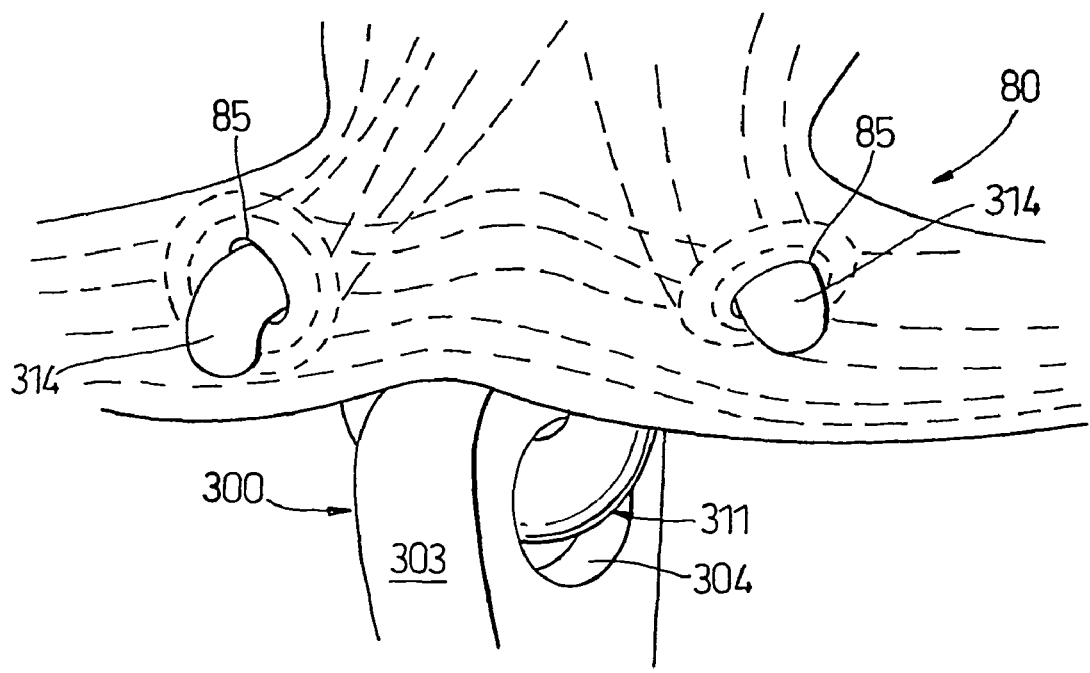
FIG. 19 is a diagrammatic view showing the modified sixth embodiment attached to the metal prosthesis of FIG. 18.

In this regard, a suitable metal prosthesis 300 is illustrated in FIG. 18 which has a body 301 intended to be attached, by for example bone screws, to a bone of the patient. The body 301 includes a flange 303 which includes at least one bore 304 passing therethrough.

An anchor member 310 is provided which has a generally U-shaped body 311 which can be inserted through a bore 304 as illustrated.

The body 311 has two arms 312 which have hook formations 314 at their terminal ends.

The hook formations 314 are spaced apart by a distance corresponding to the distance between apertures 85 to thereby enable the prosthesis 80 to be attached to the anchor member 310 by inserting the hook formations 314 into apertures 85.

Figure 20:
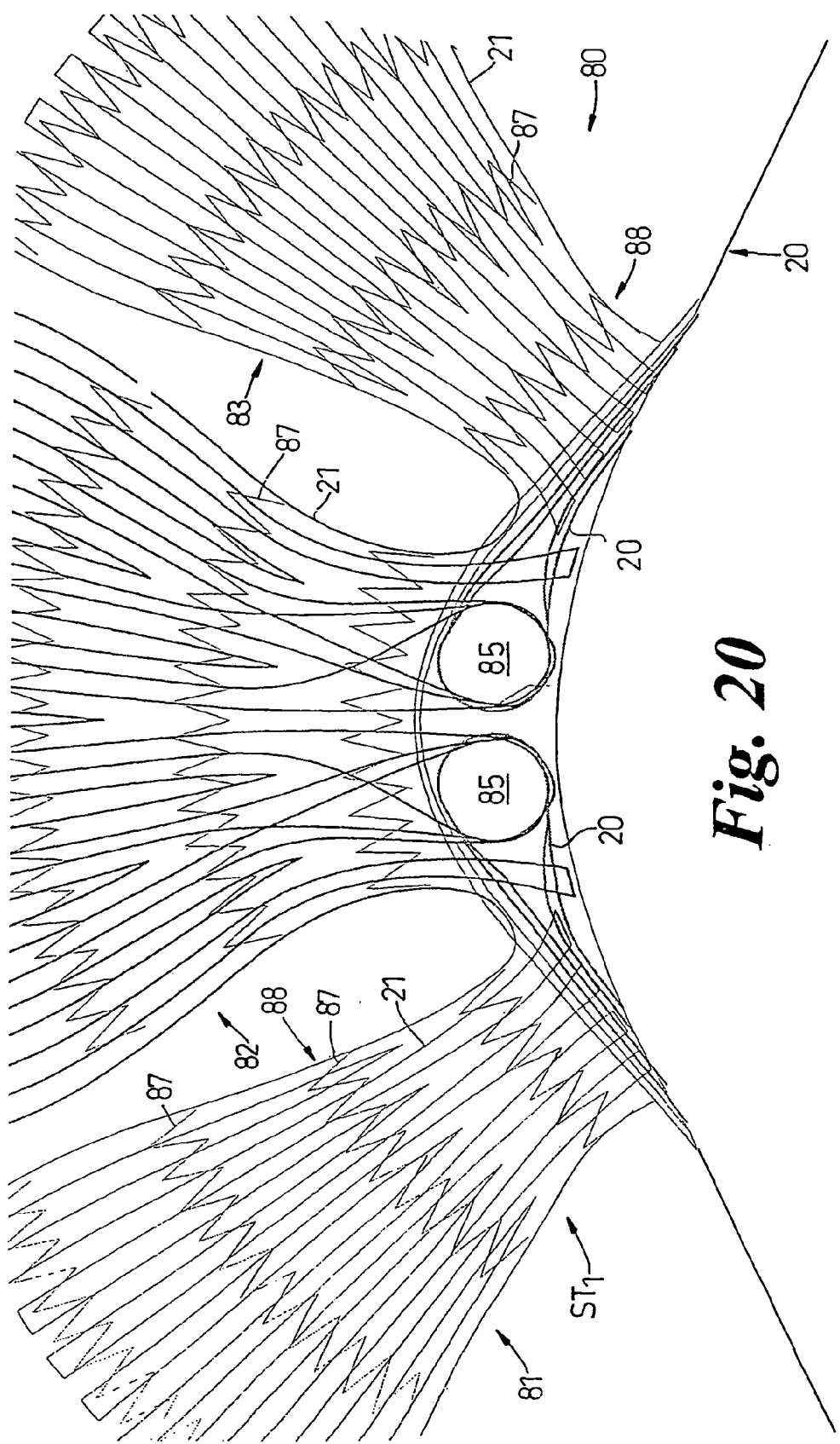
FIG. 20 is an enlarged schematic diagram of the modified sixth embodiment.

As more clearly seen in FIG. 20, the load bearing yarns 20 extending through an arm portion 90 preferably loops around the nearest aperture 85. This enables the arm portion 90 to directly transmit loads along the load bearing yarn 20 from the hook portion 314 passing through the aperture 85.

Similarly, load bearing yarns 20 which extend through the central body portion 82 also loop around apertures 85 to enable loads to be directly transmitted from the hook formations 314 and in a direction along the length of the central body portion 82.

Figure 21:
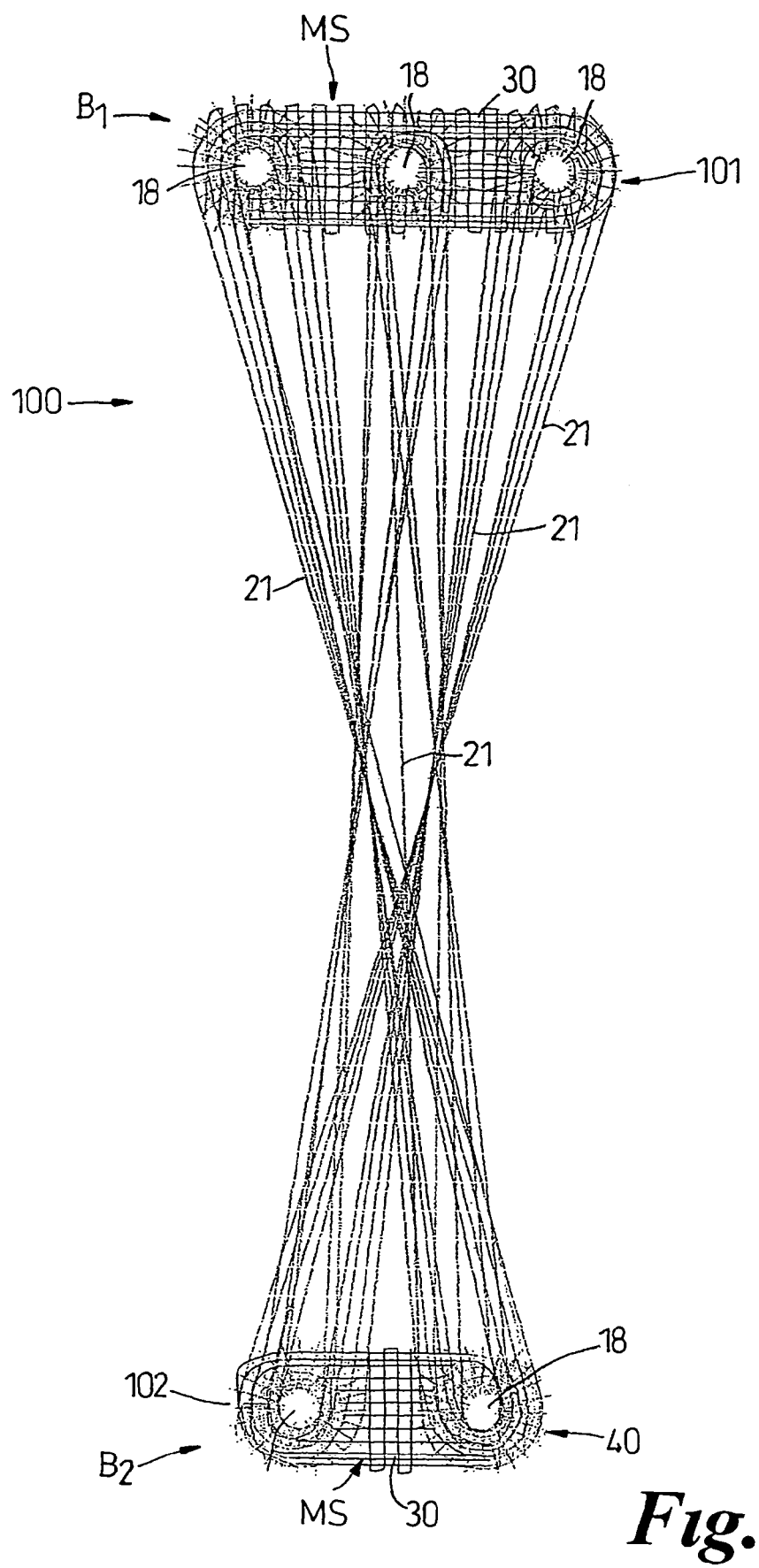
FIG. 21 is a diagrammatic plan view of a seventh embodiment according to the present invention.

Embodiment 100 illustrated in FIG. 21 comprises a body 12 having two discrete anchorage body portions $B_1$, $B_2$ defined by two body portions 101, 102 which are connected to one another only by tensile load bearing yarn length portions 21.

The yarn 20 is secured within body portions 101, 102 by star formations 40 and binding yarns 30 which preferably form a mesh-like structure MS. The yarn lengths 21 cross over from right to left and left to right as they extend between the body portions 101, 102. By suitable placement using the embroidery machine, each length portion 21 is of a predetermined length so that all length portions 21 have the same tensile load applied thereto when body portions 101, 102 are pulled part. This has the advantage that there will not be a cascade failure of one yarn length 21 breaking after another once a first one of the lengths 21 has broken.

Figure 22:
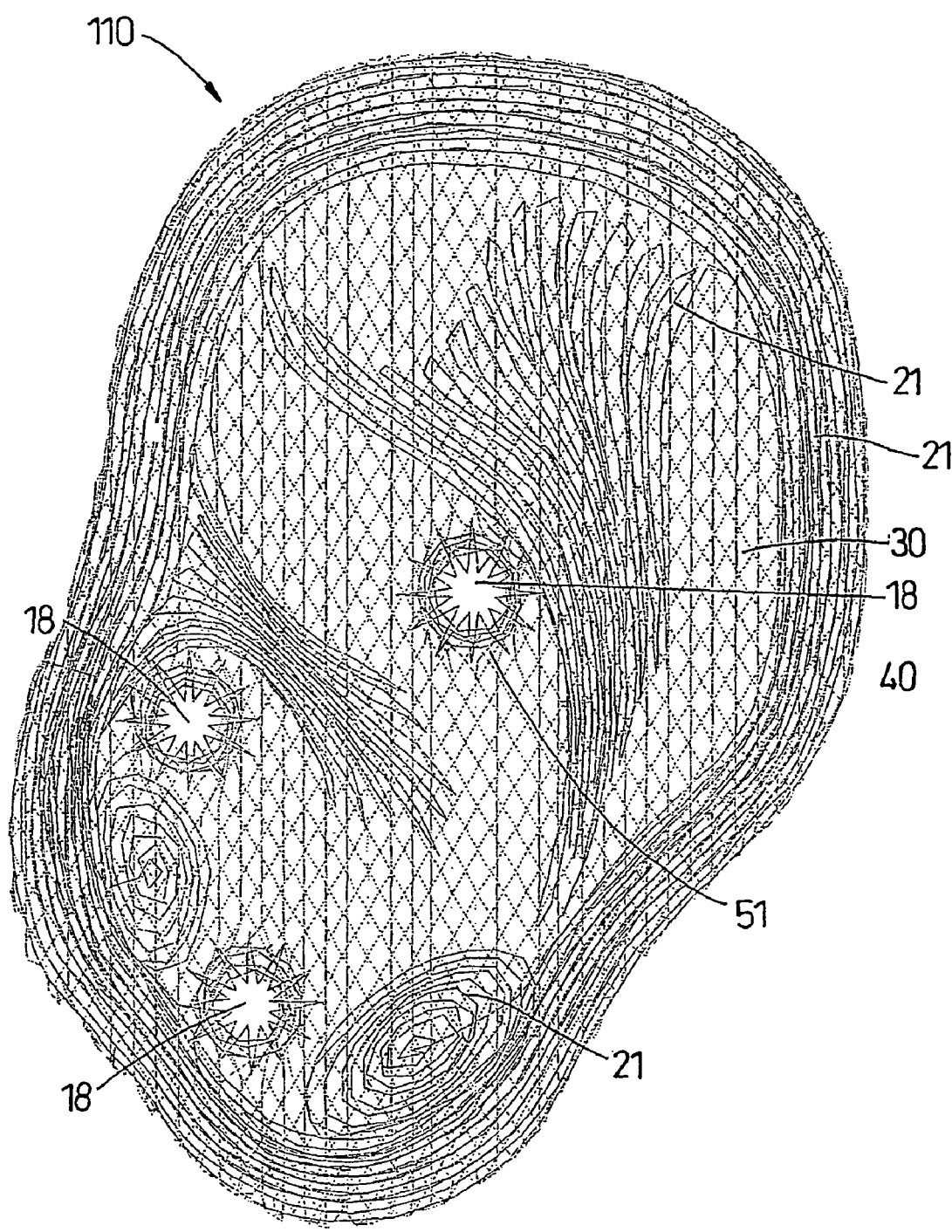
FIG. 22 is a diagrammatic plan view of an eighth embodiment according to the present invention.

Embodiment 110 illustrated in FIG. 22 is a textile prosthesis in the shape of an ear.

The prosthesis 110 includes three apertures 18 for bone screws (not shown). Each of the apertures 18 are formed by an annulus 51 and star formation 40 as described above.

Tensile load bearing yarns 20 extend through the body of the prosthesis along a predetermined circuitous path in order to provide reinforcement at desired locations and provide desired shape and volume to the prosthesis.

The prosthesis 110 may be placed in a cell culture medium to allow tissue ingrowth into the textile fabric of the prosthesis before being placed in position adjacent to the head of the patient to allow further tissue ingrowth from the body of the patient.

Figure 23:
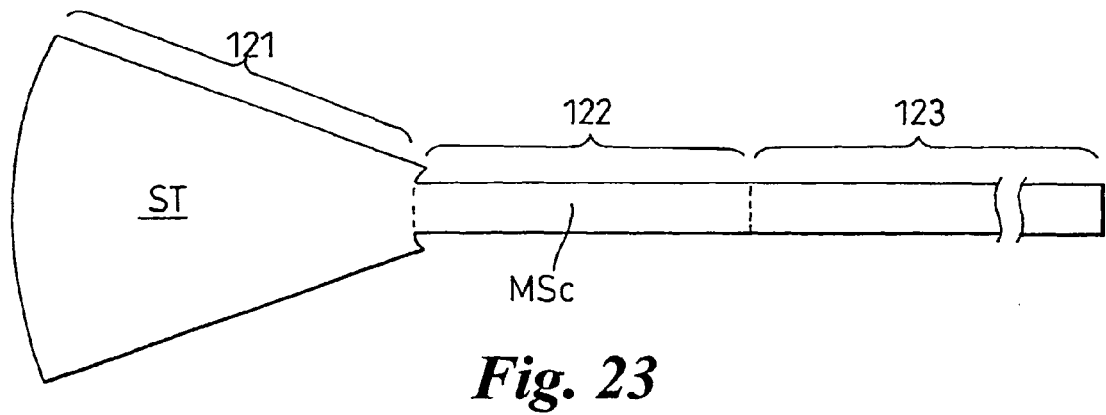
FIG. 23 is a diagrammatic plan view of a ninth embodiment according to the present invention.
Figure 24:
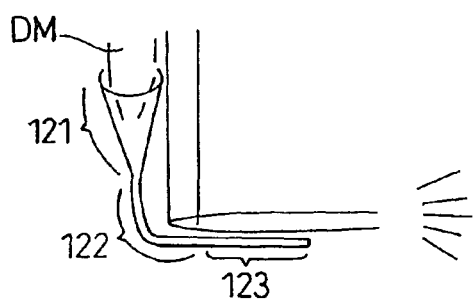
FIG. 24 is a diagrammatic sketch showing the ninth embodiment in situ.

Embodiment 120 illustrated in FIGS. 23, 24 is an example of a prosthesis according to the invention which can be used as an automotive transfer device.

The automotive transfer device of FIG. 23 is intended for generating movement about the elbow of a patient. The prosthesis includes a body 10 having a first discrete region 121, a second discrete region 122 and a third discrete region 123.

The first region 121 is defined by an anchorage body portion ST which is intended to be wrapped about and secured to the posterior deltoid muscle DM as shown schematically in FIG. 23. The anchorage portion ST is first secured by suturing and then biologically by tissue ingrowth.

The third discrete region 123 is secured to the lower arm, for example by a bone anchor or a screw.

In order to enable contractions of the posterior deltoid muscle to be translated into axial displacement of the third region 123, it is necessary for the intermediate, second discrete region 122 to remain free to move axially relative to the tissue of the patient through which it passes (typically just underneath the patients' skin). The second region 122 therefore includes a closed mesh-like structure $MS_c$ formed from binding yarns 30 which discourages tissue ingrowth.

In the above examples, when placing the tensile load bearing yarns 20, or the binding yarn 30 or forming the annuli 51 or star formations 40, the same type of yarn is used for both the sewing and looper heads of the embroidery machine. However, it will be appreciated that different yarns may be used in the sewing and looper head if desired. In addition, the yarn used for the tensile load bearing yarn 20 is preferably a polyester braided thread as used for sutures. Preferably the load bearing yarn 20 has a diametric size varying between 0.2 to 0.5 mm, more preferably is about 0.35 mm. Other types of yarn could also be used if desired, for example polypropylene, polyethylene, polyamide.

Instead of a yarn, other types of material made into filaments may be used, eg. wire of suitable metals such as a SMA (Shape Memory Alloy), aramid fibres, glass strands, etc.

In general, it is envisaged that any filament having the desired tensile load bearing capabilities and flexibility for bending to lie along a circuitous pathway may be used.

Preferably the yarn used for the binding yarns 30 is also a polyester braided thread. Preferably the binding yarn 30 has a diametric size varying between 0.1 to 0.2 mm.

It will be appreciated from the above that the present invention provides an improved method of placing fibres so as to manufacture textile prostheses, such as surgical implants (and other products), whereby the fabric structure of body portions of the prosthesis are stronger and/or have better integrity and/or have better load spreading characteristics and/or have better load concentration characteristics and/or exhibit less distortion around holes, and/or are stronger and/or distort less under load and/or creep less under load and/or have improved mesh characteristics to improve tissue ingrowth and/or have a structure intended to reduce tissue ingrowth.

Although the above embodiments are directed to textile prostheses which are primarily used for connecting parts of a body to one another, it is to be appreciated that the principles of the present invention may be used to create textile connector, in particular connectors, which can be used for connecting mechanical components together. The textile connector of the present invention may also form reinforcement for encapsulation within a matrix material, e.g. a synthetic resin, in order to form a composite component or may have elements that are encapsulated in a matrix material and elements that extend outside the matrix material, i.e. elements which are unconstrained.

The invention claimed is:

1. A prosthesis comprising a unitary body of predetermined shape having structural integrity, the body including an anchorage body portion for attachment to an anatomical body part, and being composed of a combination of binding yarns and one or more tensile load bearing filaments, the binding yarns being located in said anchorage body portion and being interconnected to one another by sewn stitches, the one or more tensile load bearing filaments being located in between said stitches so as to be constrained to extend through said unitary body along predetermined pathways extending in one or more predetermined directions so as to render the body resistant to stretch when a tensile load is applied in said one or more predetermined directions, the body further including a first aperture and a second aperture, the one or more load bearing filaments extending in a looped fashion about said first and second apertures along a fully continuous circuitous route including more than one continuous circuit to define a chain link.

2. The prosthesis according to claim 1 wherein the body includes a group of at least three apertures wherein pairs of said apertures in said group are interconnected by a chain link.

3. The prosthesis according to claim 1 wherein the one or more load bearing filaments are laid-in in between stitches of said binding yarns.

4. The prosthesis according to claim 1 wherein the one or more load bearing filaments are formed into sewn stitches which are located in between said stitches interconnecting said binding yarns.

5. The prosthesis according to claim 1 wherein said circuitous route of the one or more load bearing filaments is looped to define opposed loops.

6. The prosthesis according to claim 1 further including a second anchoring body portion defined by a planar areal portion of stretch resistive fabric formed by the binding yarns and the one or more load bearing filaments.

7. The prosthesis according to claim 6 wherein said stretch resistive fabric is adapted to promote tissue ingrowth to enable said fabric to be biologically secured to said anatomical part.

8. The prosthesis according to claim 6 wherein the one or more load bearing filaments extend continuously across a predetermined area of the fabric of the second body portion along a predetermined circuitous route.

9. The prosthesis according to claim 1 wherein at least one of said first and second apertures is formed in said anchorage body portion and dimensioned to pass a fixation element therethrough to affix the anchorage body portion to said anatomical part.

10. The prosthesis according to claim 9 wherein at least one of the first and second apertures is surrounded by a circumferential reinforcement defined by one or more load bearing filaments anchored by said binding yarns to extend at least partially around the aperture.

11. The prosthesis according to claim 10 wherein the one or more load bearing filaments of the circumferential reinforcement extends continuously around the aperture.

12. The prosthesis according to claim 10 wherein the one or more load bearing filaments of the circumferential reinforcement extends completely around the aperture.

13. The prosthesis according to claim 1 wherein the body includes at least two discrete anchorage body portions interconnected by a connecting body portion formed from said binding yarns.

14. The prosthesis according to claim 1 wherein the body includes at least two discrete anchorage body portions connected solely by the one or more load bearing filaments.

15. The prosthesis according to claim 1 wherein said anchorage body portion has an outside edge about its perimeter, and the one or more load bearing filaments begin and terminate approximate said outside edge.

16. The prosthesis according to claim 1 further including a generally planar areal portion formed of stretch resistive fabric extending from said anchorage body portion, said stretch resistive fabric formed by the binding yarns and the one or more load bearing filaments.

17. The prosthesis according to claim 1 further including a pull-string portion formed of stretch resistive fabric extending from said anchorage body portion, said stretch resistive fabric formed by the binding yarns and the one or more load bearing filaments.

18. The prosthesis according to claim 1 further including a generally planar areal portion formed of stretch resistive fabric extending from a first region of said anchorage body portion and a pull-string portion formed of stretch resistive fabric extending from a second region of said anchorage body portion, said stretch resistive fabric formed by the binding yarns and the one or more load bearing filaments.

19. The prosthesis according to claim 18 wherein at least one of said first and second apertures is formed in said anchorage body portion.

20. The prosthesis according to claim 19 wherein said first and second apertures are surrounded by a circumferential reinforcement defined by one or more load bearing filaments anchored by said binding yarns.

21. The prosthesis according to claim 20 wherein the one or more load bearing filaments of said circumferential reinforcement is further fortified by the binding yarns sewn in a generally star-shaped stitch around each of said first and second apertures.

22. The prosthesis according to claim 1 wherein the body is dimensioned for use in shoulder surgery.

23. The prosthesis according to claim 1 wherein the body is dimensioned for use in spinal surgery.

24. The prosthesis according to claim 1 including a third aperture, wherein said first, second, and third apertures are generally collinear within said anchorage body portion with a first chain-link between the first and second apertures and a second chain-link between said second and third apertures.

25. The prosthesis according to claim 1 wherein the binding yarns are selected to promote tissue ingrowth into the body.

26. The prosthesis according to claim 25 wherein the binding yarns are constructed from polyester.

27. The prosthesis according to claim 1 wherein the one or more load bearing filaments is selected to promote tissue ingrowth into the body.

28. The prosthesis according to claim 25 wherein the one or more load bearing filaments is constructed from polyester.

29. The prosthesis according to claim 1 wherein the body is created by an embroidery process.

30. The prosthesis according to claim 1 wherein at least one of the first and second aperture is fortified by binding yarns sewn in a generally star-shaped stitch around the aperture.

* * * * *